(12) United States Patent
Roth

(10) Patent No.: US 9,657,359 B2
(45) Date of Patent: May 23, 2017

(54) GENERIC ASSAYS FOR DETECTION OF MAMALIAN REOVIRUS

(75) Inventor: Bernhard Roth, Lahntal (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/821,543

(22) PCT Filed: Sep. 7, 2011

(86) PCT No.: PCT/IB2011/053921
§ 371 (c)(1),
(2), (4) Date: Aug. 14, 2013

(87) PCT Pub. No.: WO2012/032482
PCT Pub. Date: Mar. 15, 2012

(65) Prior Publication Data
US 2013/0315953 A1      Nov. 28, 2013

Related U.S. Application Data

(60) Provisional application No. 61/402,943, filed on Sep. 7, 2010.

(51) Int. Cl.
*C12Q 1/70* (2006.01)
*A61K 39/12* (2006.01)
*A61K 39/145* (2006.01)

(52) U.S. Cl.
CPC .............. *C12Q 1/70* (2013.01); *A61K 39/12* (2013.01); *A61K 39/145* (2013.01); *C12Q 1/701* (2013.01); *C12Q 2600/16* (2013.01)

(58) Field of Classification Search
USPC ........................................ 424/209.1; 435/5
See application file for complete search history.

(56) References Cited

FOREIGN PATENT DOCUMENTS

| WO | WO-94/29439 | 12/1994 | |
|---|---|---|---|
| WO | WO2006027698 | * 3/2006 | ........... A61K 39/145 |
| WO | WO-2010/067013 | 6/2010 | |

OTHER PUBLICATIONS

Spinner ML, Di Giovanni GD. Detection and identification of mammalian reoviruses in surface water by combined cell culture and reverse transcription-PCR. Appl Environ Microbiol. Jul. 2001; 67(7):3016-20.*
Leary TP, Erker JC, Chalmers ML, Cruz AT, Wetzel JD, Desai SM, Mushahwar IK, Dermody TS. Detection of mammalian reovirus RNA by using reverse transcription-PCR: sequence diversity within the lambda3-encoding L1 gene. J Clin Microbiol. Apr. 2002; 40(4):1368-75.*
Bustin SA. Absolute quantification of mRNA using real-time reverse transcription polymerase chain reaction assays. J Mol Endocrinol. Oct. 2000; 25(2):169-93. Review.*
Gadberry MD, Malcomber ST, Doust AN, Kellogg EA. Primaclade—a flexible tool to find conserved PCR primers across multiple species. Bioinformatics. Apr. 1, 2005;21(7):1263-4. Epub Nov. 11, 2004.*
Gallagher EM, Margolin AB. Development of an integrated cell culture-real-time RT-PCR assay for detection of reovirus in biosolids. J Virol Methods. Feb. 2007; 139(2):195-202. Epub Dec. 11, 2006.*
Harrison SJ, Farsetta DL, Kim J, Noble S, Broering TJ, Nibert ML. Mammalian reovirus L3 gene sequences and evidence for a distinct amino-terminal region of the lambdal protein. Virology. May 25, 1999; 258(1):54-64.*
Wellehan JF Jr, Childress AL, Marschang RE, Johnson AJ, Lamirande EW, Roberts JF, Vickers ML, Gaskin JM, Jacobson ER. Consensus nested PCR amplification and sequencing of diverse reptilian, avian, and mammalian orthoreoviruses. Vet Microbiol. Jan. 1, 2009; 133(1-2):34-42. Epub Jun. 21, 2008.*
International Search Report mailed on Feb. 14, 2012 for International Patent Application No. PCT/IB2011/053921, filed on Sep. 7, 2001.
Leary (2002). "Detection of reovirus by reverse transcription-polymerase chain reaction using primers corresponding to conserved regions of the viral L1 genome segment." J Virol Methods. 104(2):161-5.
Saito et al. (2004). "Lack of evidence for reovirus infection in tissues from patients with biliary atresia and congenital dilatation of the bile duct." J Hepatol. 40(2):203-11.
Kohl et al. (2012). "Isolation and Characterization of Three Mammalian Orthoreoviruses from European Bats." PLoS ONE 7(8): e43106.

* cited by examiner

*Primary Examiner* — Angela M Bertagna
*Assistant Examiner* — Olayinka Oyeyemi
(74) *Attorney, Agent, or Firm* — Morrison & Foerster LLP

(57) ABSTRACT

The invention relates to generic methods for the detection and quantification of mammalian reoviruses. These may uses a reverse transcription (RT-PCR) real time (q-PCR) assay which amplifies a conserved region within all MRV types. The assays allow the quantification of MRV RNA molecules, irrespective of the particular virus type (e.g. MRV-1, MRV-2). The methods are particularly applicable in the monitoring of vaccine production processes.

11 Claims, 3 Drawing Sheets

FIG. 2

```
                        (2024) 2024    2030         2040
       Reovirus 1 Lang(2023)  TCAATCGAGACGCGCGAGTG
      Reovirus 2 Jones(2023)  TCAATCACGGAGAGCTAGCG
   Reovirus 3 Dearing(2023)   TCAATCGAGACGCGCGAGTG
              Consesus(2024)  TCAATCGAGACGCGCGAGTG
``` mRV BR1F

→

```
         2050         2060         2070
  CTTTCTCAACGCCTCACACGTGGCCACGATGCTT
  CGTTTTCCACTCCCCACACTTGGCCACGATGCTT
  CTTTCTCAACGCCTCACACGTGGCCACGATGCTT
  CTTTCTCAACGCCTCACACGTGGCCACGATGCTT
``` mRV LNA2

-------------->

```
    2080         2090         2100         2110
  CATGAATATCCAGTTAATTTCTCCAATCGATGCTCCTATCT
  TATGAACATACAATTGATTTCGCCAATCGACGCTCCAATCC
  TATGAACATCCAGTTAATTTCTCCAATCGACGCTCCCATCT
  TATGAACATCCAGTTAATTTCTCCAATCGACGCTCC ATCT
``` mRV rev

←

```
   2120       2130       2140       2150      2161
  TGCGACAGTGGGCTGAAATTATTCATAGATACTGGCCTAACCC
  TGAGACAGTGGGCCGAGATTATTCATAGATACTGGCCGAATCC
  TGCGACAGTGGGCTGAAATTATTCATAGATACTGGCCTAACCC
  TGCGACAGTGGGCTGAAATTATTCATAGATACTGGCCTAACCC
```

GENERIC ASSAYS FOR DETECTION OF MAMALIAN REOVIRUS

RELATED APPLICATIONS

This application is the U.S. National Phase of International Application No. PCT/IBUS2011/053921, published in English, and claims the benefit of U.S. Provisional Patent Application No. 61/402,943 tiled on Sep. 07, 2010, the entire teachings of which are incorporated herein by reference.

TECHNICAL FIELD

The present invention relates to novel, generic methods for the detection and quantification of mammalian reoviruses (MRV). The invention preferably uses a reverse transcription (RT-PCR) Real Time (q-PCR) assay which amplifies a conserved region within the MRV genome. The inventive assays allow the quantification of viral RNA molecules, irrespective of the particular virus type (e.g. MRV-1, MRV-2, MRV-3 etc.). The methods of the invention are particularly applicable in the monitoring of vaccine production processes, especially in production and quality control of influenza virus vaccines.

BACKGROUND OF THE INVENTION

Methods for detecting contamination by adventitious agents in mammalian cell culture for influenza vaccine production are described in reference 1. These contaminating viruses include mammalian Reoviridae, in particular orthoreoviruses (e.g. mammalian reoviruses—MRV), which would be able grow particularly well in the MDCK cells used for Optaflu™ vaccine production were they to become contaminated. At present, however, there is no available PCR method to detect MRV that is acceptable in terms of specificity and sensitivity for the purpose of quality control of influenza vaccine production.

Two known mammalian reovirus PCR assays [2, 3] have been tested by the inventors for suitability for the purpose of quality control of influenza vaccine production.

Reference 2 describes a nested PCR method, in which the first PCR with primers L1.rv5 and L1.rv6 amplify a conserved 416 bp product of the L1 gene. The nested PCR with primers L1.rv7 and L1.rv8 amplify a conserved 344 bp product of the L1 gene. The present inventor has found that, in the method described in reference 2, the first PCR yielded nonspecific products with some strains and the nested PCR was sufficiently sensitive and specific only for the MRV-1 strain Dearing and MRV-2 strain Lang. Furthermore, he found that there was reduced performance and nonspecific products with MRV-3 strain Jones.

Reference 3 describes a RT-PCR method to detect a region in the L3 inner capsid gene. The present inventor found that this method provides a low yield with significant contamination from primer-dimers.

The results of the analysis of the methods of references 2 and 3, and of the present invention, are shown in FIG. 1.

There therefore remains a need for a specific and sensitive generic method to detect and quantify all MRV types.

DISCLOSURE OF THE INVENTION

In contrast, the present invention allows for the detection of all types and strains of MRV with high sensitivity and specificity. The present invention provides:

A method for detecting MRV RNA, and in particular simultaneous detection of MRV-1, MRV-2 and MRV-3 RNA Primers, probes and kits for the detection of MRV RNA, and in particular for simultaneous detection of MRV-1, MRV-2 and MRV-3 RNA using a single primer pair and probe A method of confirming that an influenza vaccine is, or is not, free from contamination with MRV An influenza vaccine that has been confirmed as free from the presence of MRV A method of producing an influenza vaccine comprising the step of detecting the presence or absence of MRV RNA

METHODS OF THE INVENTION

The present invention provides a method for detecting the presence or absence of MRV RNA, and in particular MRV-1, MRV-2 and MRV-3 RNA. The methods of the present invention analyze a conserved region within the MRV genome. By "conserved region" it is meant a region with a high degree of sequence identity between MRV subtypes, for example 100%, or at least 99.5%, 99%, 98%, 95% or 90% sequence identity between MRV-1, MRV-2 and MRV-3 when the respective regions are aligned. The conserved region may be from about 200 to about 20 bases in length, for example $\geq 190$, $\geq 180$, $\geq 170$, $\geq 160$, $\geq 150$, $\geq 140$, $\geq 130$, $\geq 120$, $\geq 110$, $\geq 100$, $\geq 90$, $\geq 80$, $\geq 70$, $\geq 60$, $\geq 50$, $\geq 40$, or $\geq 30$ bases in length. Preferably the conserved region is within the region encoding the L3 inner capsid protein. Previous attempt have been made to develop a generic MRV assay using conserved sequence in the region encoding the L1 gene [2] and the L3 gene [3], but these have not led to a reliable assay for different MRV types.

The L3 inner capsid gene nucleotide sequences which were used for an alignment of the MRV-1, MRV-2 and MRV-3 genes in the present invention are shown in FIG. 2.

The invention provides a method for simultaneously detecting the RNA genome of any MRV type, subtype and strain in a single assay. In particular, the assay can simultaneously detect MRV-1, MRV-2 and MRV-3 RNA. In a specific embodiment, the assay is capable of detecting at least MRV-1 Lang strain (ATCC VR-230; L3 sequence Genbank GI:23307868), MRV-2 Jones strain (ATCC VR-231; L3 sequence Genbank GI:23307891) and MRV-3 Dearing strain (ATCC VR-824; L3 sequence Genbank GI:23309022).

The methods of the present invention are able to detect the presence of all MRV types, subtypes and strains with a detection limit of $\leq 100$ $TCID_{50}$/ml, $\leq 80$ $TCID_{50}$/ml, $\leq 50$ $TCID_{50}$/ml, $\leq 35$ $TCID_{50}$/ml or $\leq 10$ $TCID_{50}$/ml. Alternatively, the detection limit can be defined in terms of viral genomes or virions per ml of sample. The methods of the present invention are able to detect the presence of all MRV types, subtypes and strains with a detection limit of $\leq 200$ genome copies or virions per ml, $\leq 100$ genome copies or virions per ml, or $\leq 50$ genome copies or virions per ml.

Thus, a negative result in the methods of the present invention can be taken to indicate that the sample is substantially free from MRV.

The invention also provides a method of confirming that a sample is, or is not, substantially free from the presence of MRV, comprising detecting the presence or absence of MRV RNA using the methods of the invention described above.

By "substantially" it is meant that there is no detectable MRV in the sample when using the detection methods of the invention, i.e. the sample contains ≤100 TCID$_{50}$/ml, ≤80 TCID$_{50}$/ml, ≤50 TCID$_{50}$/ml, ≤35 TCID$_{50}$/ml or ≤10 TCID$_{50}$/ml MRV or alternatively the sample contains ≤200 genome copies or virions per ml, ≤100 genome copies or virions per ml, or ≤50 genome copies or virions per ml.

In one embodiment, the sample is an influenza vaccine or an intermediate in the manufacture of an influenza vaccine.

In one embodiment, the invention provides a method for detecting the presence or absence of MRV RNA comprising the steps of:
  (a) extracting RNA from a sample;
  (b) performing a nucleic acid assay using the RNA extracted in step (a) to amplify a conserved region within the MRV genome; and
  (c) detecting the presence or absence of the MRV RNA using the product of step (b).

Nucleic Acid Detection

The detection methods of the present invention can be used to identify the presence or absence of an MRV nucleic acid in a sample. A positive result is the detection of the presence of an MRV nucleic acid in the sample. A negative result is the absence of the detection of an MRV nucleic acid in the sample. In one embodiment, the negative result is confirmed to be due to the absence of a MRV nucleic acid in the sample rather than a failure of the assay, i.e. the assay has successfully detected the presence of positive control nucleic acids but not an MRV nucleic acid in the sample. Given that the present invention is directed in part to ensuring that influenza vaccines are free from contamination from MRV, the assays of the invention will predominantly be used to detect or confirm the absence of MRV RNA.

Nucleic acids can be extracted from samples, and in particular from the MRV virions in the samples by any method that is suitable for extracting RNA from non-enveloped, double-stranded RNA viruses. Various methods are known in the art and several products for their performance are commercially available. In one embodiment, the nucleic acids are isolated from MRV particles using the commercially automated RNA/DNA system MagNA Pure Compact System (Roche) with the MagNA Pure Compact Nucleic Acid Isolation Kit (Roche). Virions may be lysed by incubation of the samples with lysis buffer containing protease K. Alternatively, viral nucleic acids may be extracted from MRV using a QIAamp viral RNA kit (Qiagen, Valencia, Calif.) according to the manufacturer's directions.

For the amplification and/or detection, a nucleic acid assay is conducted. A preferred assay is Reverse Transcriptase Polymerase Chain Reaction (RT-PCR). However, equivalent RNA amplification methods are also applicable, as known to the person skilled in the art (Nucleic Acid Sequence Based Amplification or NASBA™ as in U.S. Pat. No. 5,409,818; 3SR™; Transcription Mediated Amplification or TMA™ as in U.S. Pat. No. 5,399,491 etc.). The nucleic acid assay is preferably run as a real time assay (e.g. "qPCR"; Taqman™, Lightcycler™; Scorpion™ etc.). Preferably, the nucleic acid assay is performed using the primer and/or probe sequences shown in table 1 below. In a specific embodiment, the primers with SEQ ID NO: 1 and SEQ ID NO: 2 are used.

In a particular embodiment, a one step RT-real time PCR assay is used ("one step RT-qPCR"). The person skilled in the art is familiar with conducting such "one step RT qPCR" assays. He knows how to find detailed reaction conditions for such amplification. In particular, when using RNA from double-stranded RNA viruses, such as MRV, a person skilled in the art is aware that a denaturation step must precede the reverse transcription reaction.

In the present invention, the reverse transcription reaction or equivalent RNA amplification method can be carried out on either the positive strand, the negative strand or on both strands simultaneously. Thus, the methods of the invention can be used to detect the positive and/or negative strand of the MRV nucleic acid.

The reverse transcription reaction (RT) and the amplification reaction (qPCR) may be performed in the same vessel (e.g. in a single tube or vial) rather than in separate vessels. Commercially available RT-PCR kits can be used, e.g. Qiagen QuantiTect™ Virus kit or Invitrogen Super Script™ III Platinum™ kit. The generated fluorescence signals can be analyzed using the respective real time cycler software, as known in the art. When using a method that involves qPCR, the amount of MRV nucleic acid in a sample can be quantified. For example, it is possible to determine the number of viral genomes or virions present in the sample.

In an alternative embodiment, RT-PCR followed by hybridization with a probe or followed by agarose gel electrophoresis can be used to detect the viral nucleic acids. RT-PCR products can be visualized in the agarose gel using ethidium bromine. The reverse transcription and PCR reactions may be carried out in the same or separate vessels.

The inventive nucleic acid assays can be quantified by comparing the generated fluorescence signal with the respective signal of a standard nucleic acid, as known in the art. One such standard is an in vitro transcript (IVT), which can be used as a control. In one embodiment, a dilution series of the IVT is used as a control. In one embodiment, an IVT of the respective virus regions is used. Suitable IVTs can be generated as required or, if the IVT is not derived from the respective virus region, commercially available IVTs can be used e.g. Panomics™ supplies "Ifn-A" (282 nucleotides) and "Ifn-B" (276 nucleotides) single-stranded RNA molecules at 10 ng/ml.

Preferably, RT-qPCR is performed using the primer and/or probe sequences shown in table 1 below. In a specific embodiment, the primers comprise or consist of SEQ ID NO: 1 and SEQ ID NO: 2. In a further specific embodiment, the probe comprises or consists of SEQ ID NO: 3.

In a particular preferred embodiment, the primers of SEQ ID NO: 1 and SEQ ID NO: 2 are combined with the probe of SEQ ID NO: 3 for the detection of all MRV types. The examples (see below) show that the one step RT qPCR assay of the invention is capable of detecting MRV of different origins.

The person skilled in the art knows how to design additional primers and probes directed to the virus genome encoding the L3 inner capsid protein or to other conserved regions within the MRV genome. The person skilled in the art knows that the Taqman probes shown in the table below can be substituted by equivalent Lightcycler probes or other real time probe systems.

Sequences and Kits

The methods of the invention may be carried out using of primers and probes that are specific for the MRV L3 inner capsid gene sequence. By "specific" with reference to a primer, it is meant that any particular primer pair, containing one forward and one reverse primer, will give rise to a single amplification product when the template is a nucleic acid from a single strain of MRV, and will not give rise to any amplified product when the template is an avian reovirus nucleic acid. By "specific" with reference to a probe, it is meant that the probe will hybridize only with the amplified MRV nucleic acid sequence from the amplification reaction and does not hybridize with other MRV nucleic acid sequences or with an avian reovirus nucleic acid. The invention also encompasses the primer and probe sequences outlined in Table 1 (SEQ ID NOs: 1, 2 and 3). Further details of primer and probe design are provided in the section entitled "Primer and probe design" below.

An example of a forwards primer is SEQ ID NO: 1, an example of the reverse primer is SEQ ID NO: 2, and a useful probe is SEQ ID NO: 3. The term 'forwards' is used only for convenience and refers to a primer having the same sense as the ATG-containing coding strand for the L3 inner capsid protein.

The primer sequence given in SEQ ID NO: 1 includes one degenerate base and so may be present as two separate and individual oligonucleotide sequences. The primer sequence given in SEQ ID NO: 2 includes two degenerate bases and so may be present as four separate and individual oligonucleotide sequences. The probe sequence given in SEQ ID NO: 3 includes also includes two degenerate bases and so may be present as four separate and individual oligonucleotide sequences. The degenerate oligonucleotides may be present in equimolar concentrations when used in the methods of the invention.

Primer pair sequences of the present invention are preferably designed to minimize primer dimer formation. Primer pairs of the invention therefore lack complementarity between the forward and reverse primer sequences, particularly at the 3' end of the primer sequence. It is particularly important that primer pairs are designed to avoid primer dimer formation at the temperature of the reverse transcription reaction.

Primers of the present invention used in the reverse transcription reaction, in both one-step and two-step RT-PCR methods, are capable of amplifying both RNA strands from MRV with comparable efficiency and are also capable of amplifying RNA from all MRV types, subtypes and strains with comparable efficiency.

In one embodiment, the primers of the invention are designed so that the fragment amplified by a specific primer pair is ≤about 150 bases in length, e.g. from about 150 to about 50 nucleotides long including the primer sequences. In a specific embodiment, the amplified fragment may be about 140 bases, 130 bases, 120 bases, 110 bases, 100 bases, 90 bases, 80 bases, 70 bases, or 60 bases long including the primer sequences.

Primers and/or probes of the invention (e.g. SEQ ID NOs: 1-3) may be labeled e.g. with a radiolabel, a fluorescent label such as 5' 6-carboxyfluorescein (6FAM) label and/or a 3' 'BlackBerry Quencher' (BBQ) label or any other label known in the art. Probes may be locked nucleic acid (LNA) oligonucleotides that contain a cytosine modified with a 2'-O, 4'-C methylene bridge in its ribose conferring enhanced hybridization performance (shown as +C in table 1).

The invention also provides nucleic acids which comprise a nucleotide sequence selected from SEQ ID NOs 1, 2 and 3. These nucleic acids should be single-stranded with a length of less than 80 nucleotides e.g. less than 50 nucleotides, or less than 30 nucleotides. They can be useful as primers and/or probes for detecting MRV. The nucleic acid may have the same 3' residue as the relevant SEQ ID NO: i.e. it may comprise a sequence 5'-X—Y-3' where: Y is a sequence selected from SEQ ID NOs 1, 2 and 3; and X is a nucleotide sequence of 1 or more nucleotides. The nucleic acid with sequence 5'-X—Y-3' can hybridize to a MRV L3 inner capsid nucleic acid.

The invention also provides kits for the detection of MRV RNA. The kits of the invention comprise one or more primer pairs and/or probes of the invention. The kit might contain further components, e.g. buffers, polymerases and further reaction components for the amplification.

Influenza Vaccine Production

The assays of the invention are particularly useful for cell-culture based influenza vaccine production (for review see reference 4). The invention can be used at different steps during vaccine production, in particular in order to monitor contamination at all stages of the process. The inventive process is in principle suitable for the monitoring the production of various forms of influenza vaccines (e.g. live virus, inactivated whole virions, split virions, purified surface antigens; for details see reference 5). In these methods, virions are grown in and harvested from virus containing fluids, e.g. allantoic fluid or cell culture supernatant.

In one embodiment, the invention is used in cell-culture based influenza vaccine production. Suitable cell lines are described e.g. in reference 5. The most preferred cell lines for growing influenza viruses are MDCK cell lines. The original MDCK cell line is available from the ATCC as CCL-34, but derivatives of this cell line and other MDCK cell lines may also be used. For instance, in WO97/37000 a MDCK cell line is disclosed that was adapted for growth in suspension culture ('MDCK 33016', deposited as DSM ACC 2219). Similarly, WO01/64846 discloses a MDCK-derived cell line that grows in suspension in serum-free culture ('B-702', deposited as FERM BP-7449). WO2006/071563 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). WO2005/113758 discloses MDCK cell lines with high susceptibility to infection, including 'MDCK.5F1' cells (ATCC CRL-12042). Any of these MDCK cell lines can be used.

The cell culture based vaccine production process usually comprises the following steps: The starting material for each monovalent bulk is a single vial of the MDCK working cell bank (WCB). The cells are propagated in a chemically defined medium to optimize cell growth during production. The WCB are expanded by sequential passage in spinner flasks followed by scale up in larger fermentation vessels. Seed virus is added and virus propagation in the fermenter is performed over a period of two to four days. At the end of the infection cycle, the virus suspension is centrifuged and filtered to remove residual intact cells from the culture harvest. The centrifuged, filtered bulk termed clarified virus harvest is the end of the fermentation process. The clarified virus harvest may be stored at room temperature (16-25° C.) in a stainless steel storage vessel for up to 24 hours. The influenza virus is purified by chromatography and ultra-/diafiltration steps, inactivated by beta-propiolactone (BPL) and disrupted by cetyltrimethylammonium bromide (CTAB) to solubilize the viral surface antigens HA and NA. The drug substance production process concludes with a filtration of the concentrate into the final bulk vessel to obtain monovalent bulk. Finally, the monovalent bulks can be blended into multivalent bulks (typically trivalent bulks) and filled into their final container, e.g. syringes. It is standard practice to minimize the amount of residual cell line DNA in the final vaccine, in order to minimize any oncogenic activity of the DNA (see in detail reference 5).

The detection method of the invention may be performed at any stage(s) during vaccine manufacture, starting from the seed virus and/or the cell substrate and/or the culture medium, through the viral infection and growth stages, through viral harvest, through any viral processing (e.g. splitting and/or surface protein extraction), through vaccine formulation and then to vaccine packaging. Thus the assay used according to the invention can be performed on the materials used to create the viral culture, on the viral culture itself, and on material extracted and derived from the viral culture. The assay need not be performed on each and every vaccine or culture, but can be used at appropriate intervals as part of normal quality control. It is particularly useful when vaccine production is changed for the new yearly strains recommended by regulatory authorities, at which stage new cultures are established and must be subjected to new quality control. Assays of the invention are advantageously performed on the seed virus used for vaccine manufacture.

The invention also provides a method of producing an influenza virus vaccine comprising the step of detecting the presence or absence of MRV RNA using a method or kit of the invention. As described above, the detecting step may be carried out at any point during vaccine production.

The method of producing the influenza virus vaccine may comprise the steps of:
(a) infecting a culture host with influenza virus;
(b) culturing the host to produce influenza virus;
(c) purifying the influenza virus from the culture; and
(d) preparing a vaccine from the purified influenza virus.

The Influenza Vaccine

The invention concerns quality control of influenza vaccines. The methods of the invention are capable of detecting MRV in the presence of influenza virus. In one embodiment, the methods of the invention are capable of detecting MRV in the presence of $\geq 100$-fold, $\geq 1000$-fold, $\geq 10^4$-fold, $\geq 10^5$-fold or $\geq 10^6$-fold excess of influenza virus. For example, the methods of the invention can detect 2.80 log10 $TCID_{50}$/ml MRV in up to 8.1 log10 $TCID_{50}$/ml influenza virus. The invention provides an influenza vaccine that has been confirmed to be substantially free from the presence of MRV. By "substantially" it is meant that there is no detectable MRV in the influenza vaccine when using the detection methods of the invention, i.e. the sample contains $\leq 100$ $TCID_{50}$/ml, $\leq 80$ $TCID_{50}$/ml, $\leq 50$ $TCID_{50}$/ml, $\leq 35$ $TCID_{50}$/ml or $\leq 10$ $TCID_{50}$/ml MRV or alternatively the sample contains $\leq 200$ genome copies or virions per ml, $\leq 100$ genome copies or virions per ml, or $\leq 50$ genome copies or virions per ml. In a preferred embodiment, the influenza vaccine is completely free from the presence of MRV.

The vaccine may be in the form of a live virus or, preferably, an inactivated virus. Virus inactivation typically involves treatment with a chemical such as formalin or β-propiolactone. Where an inactivated virus is used, the vaccine may be a whole virus, a split virus, or viral subunits. Split viruses are obtained by treating virions with detergents (e.g. ethyl ether, polysorbate 80, deoxycholate, tri-N-butyl phosphate, Triton X-100, Triton N101, cetyltrimethylammonium bromide, etc.) to produce subvirion preparations. Subunit vaccines comprise the influenza surface antigens haemagglutinin and neuraminidase. Influenza antigens can also be presented in the form of virosomes [6].

Influenza vaccines of the invention can be based on any suitable strain(s). Vaccines typically include antigens from at least one strain of influenza A virus and/or at least one strain of influenza B virus. The recommended strains for vaccines change from season to season. In the current inter-pandemic period, vaccines typically include two influenza A strains (H1N1 and H3N2) and one influenza B strain, and trivalent vaccines are preferred. The invention is also suitable for preparing viruses from pandemic strains, such as H5 or H7 strains, that is strains to which the human population is immunologically naïve. Vaccines in pandemic situations may be monovalent, or they may be based on a normal trivalent vaccine supplemented by a pandemic strain.

The influenza virus(es) used in the processes of the invention may be reassortant strains, and/or may have been obtained by reverse genetics techniques. The virus(es) may be attenuated. The virus(es) may be temperature-sensitive. The virus(es) may be cold-adapted.

Where a vaccine includes more than one strain of influenza, the different strains are typically grown separately and are mixed after the viruses have been harvested and antigens have been prepared. Thus the processes of the invention may include the step of mixing antigens from more than one influenza strain. Testing for MRV may be performed before or after such mixing.

The vaccine will typically be prepared for administration to a patient by injection (e.g. subcutaneous injection or intramuscular injection), although other routes of administration are known for influenza vaccines e.g. intranasal [7-9], oral [10], intradermal [11,12], transcutaneous, transdermal [13], etc.

Vaccines prepared according to the invention may be used to treat both children and adults. Influenza vaccines are currently recommended for use in pediatric and adult immunisation, from the age of 6 months. Safety concerns are most acute for pediatric vaccines, particularly as immunologically naive subjects typically receive two vaccine doses in a short period (e.g. at a 1 or 2 month interval).

Vaccines of the invention may include an adjuvant. Adjuvants that have been used in influenza vaccines include aluminium salts [14,15], chitosan [16], CpG oligodeoxynucleotides such as CpG 7909 [17], oil-in-water emulsions such as MF59 [18], water-in-oil-in-water emulsions [19], E. coli heat labile toxin [8,20] and its detoxified mutants [21-22], monophosphoryl lipid A [23] and its 3-o-deacylated derivative [24], pertussis toxin mutants [25], muramyl dipeptides [26], etc.

Haemagglutinin (HA) is the main immunogen in inactivated influenza vaccines, and vaccines doses are standardised by reference to HA levels, typically as measured by a single radial immunodiffution (SRID) assay. Vaccines typically contain about 15 μg of HA per strain, although lower doses are also used e.g. for children, or in pandemic situations. Fractional doses such as ½ (i.e. 7.5 μg HA per strain), ¼ and ⅛ have been used [14, 27]. Thus vaccines may include between 1 and 150 μg of HA per influenza strain, preferably e.g. about 15, about 10, about 7.5, about 5, about 3.8, about 1.9, etc.

The vaccines may include preservatives such as thiomersal or 2-phenoxyethanol. It is preferred, however, that the vaccine should be substantially free from (i.e. less than 5 μg/ml) mercurial material e.g. thiomersal-free [28, 29]. Vaccines containing no mercury are more preferred.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Further details on MRV, including details of its life cycle during viral growth, can be found in chapter 53 of reference 30.

References to a percentage sequence identity between two sequences means that, when aligned, that percentage of monomers are the same in comparing the two sequences. This alignment and the percent homology or sequence identity can be determined using software programs known in the art, for example those described in section 7.7.18 of reference 31. Identity between amino acid or nucleotide sequences is preferably determined by the Smith-Waterman homology search algorithm [32], using an affine gap search with default parameters gap open penalty=12 and gap extension penalty=1. The BLOSUM62 scoring matrix can be used.

BRIEF DESCRIPTION OF THE DRAWINGS

FIG. 2 Nucleotide sequence alignment of the MRV PCR target region (SEQ ID NOs: 5, 6 and 7). Reovirus 1 Lang corresponds to SEQ ID NO:5, Reovirus 2 Jones corresponds to SEQ ID NO: 6, and Reovirus 3 Dearing corresponds to SEQ ID NO:7. The consensus sequence SEQ ID NO: 8 is shown below the aligned sequences.

MODES FOR CARRYING OUT THE INVENTION

Primer and Probe Design

Figure 1A:
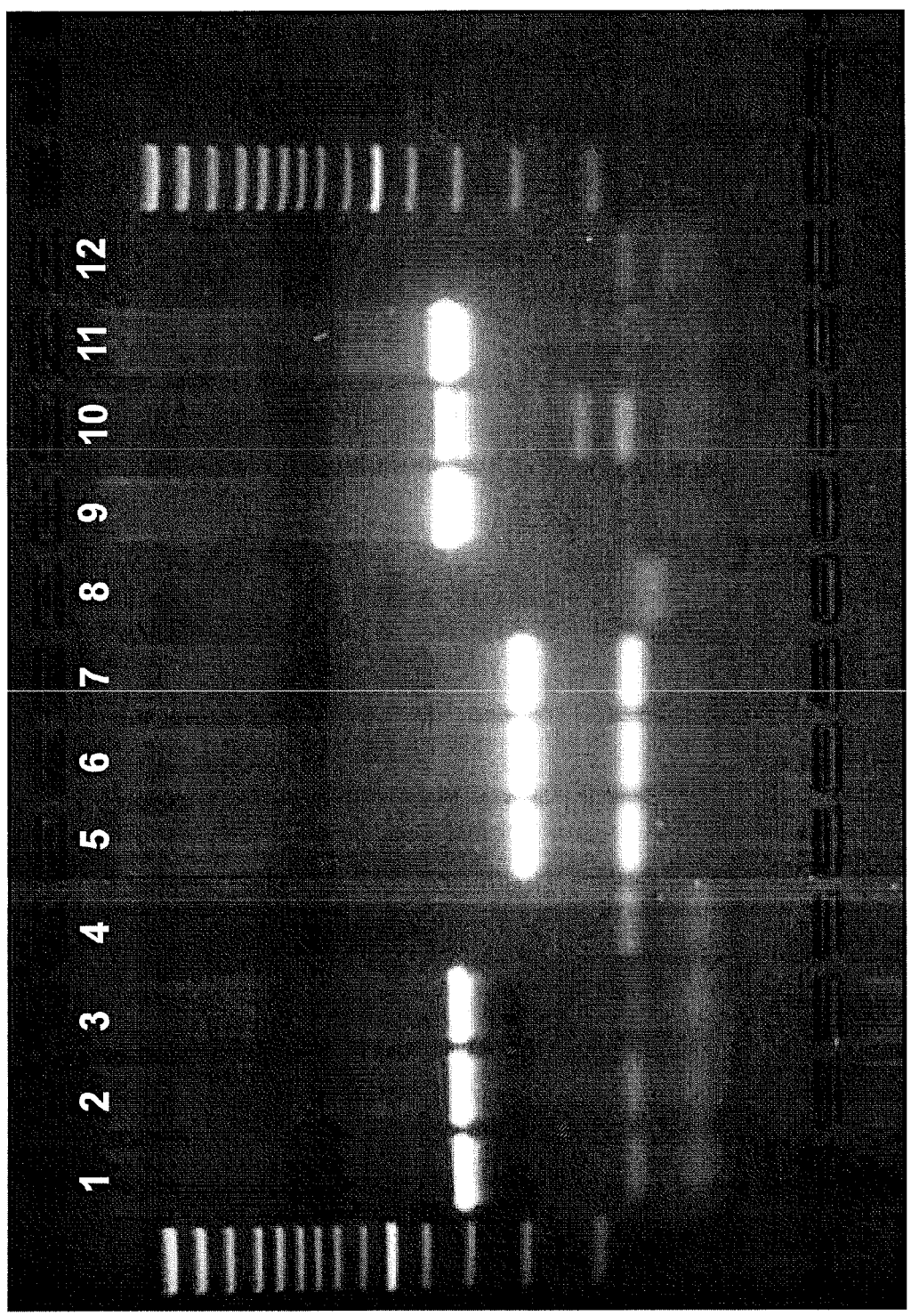
FIG. 1 Four different PCR methods were setup according to the published methods. Each numbered lane of the 1.8% agarose gel was loaded with 20 μl of the PCR product (order: MRV1/strain Lang, MRV2/strain Jones, MRV3/strain Dearing, no templatecontrol) Lanes 1-4: Spinner et al. primers [3]; lanes 5-8 NVD designed primers; lanes 9-12 Leary et al. nested primers and lanes 13-16 Leary et al. 1st PCR primers [2].
Figure 1B:
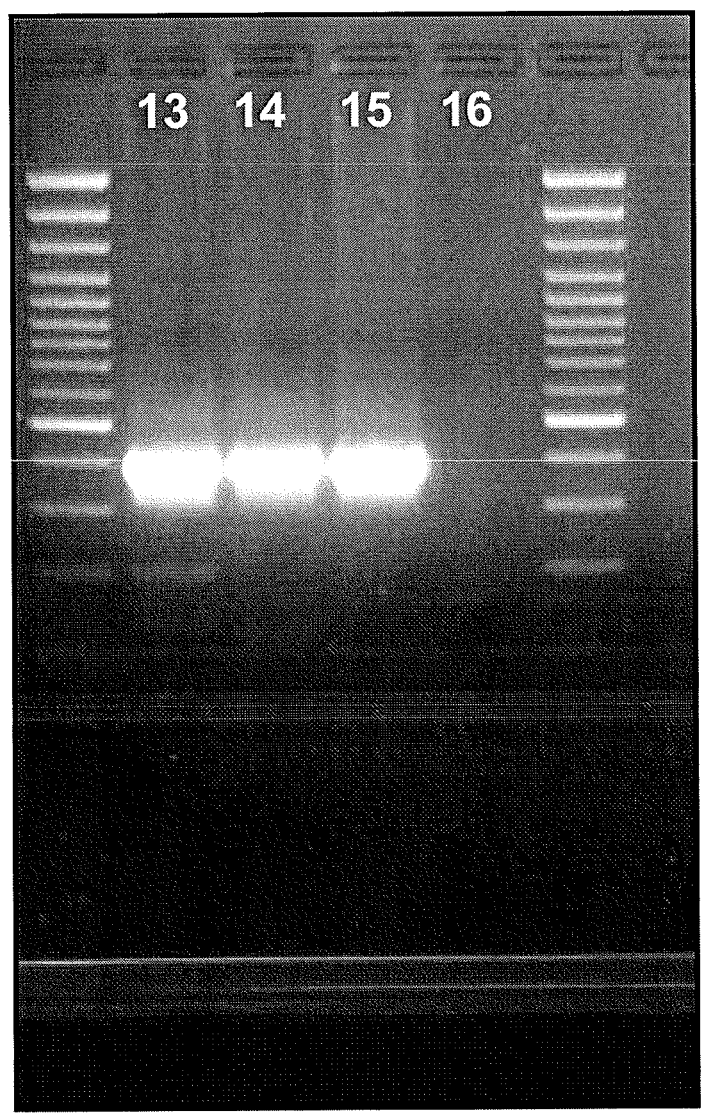

The design of the mammalian reovirus reverse transcriptase PCR assay was optimized to specifically detect MRV serotypes 1, 2 and 3 and to minimize the formation of primer dimers. Primers MRV BR1F (SEQ ID NO: 1) and MRV_rev (SEQ ID NO: 2) amplify a 89 bp sequence (SEQ ID NO: 4) from the L3 inner capsid gene in the MRV genome (FIG. 2—SEQ ID NOs: 5, 6 and 7; consensus sequence SEQ ID NO: 8). Sequence alignments of the MRV reference strains of serotype 1, 2 and 3 revealed that there are conserved regions of the MRV genome in the L3 inner capsid gene (Genbank accession codes: NC_004255 strain Lang, NC_004256 strain Jones, NC_004256 strain Dearing; see FIG. 2). Despite previous failures in using conserved genome regions to provide a specific and sensitive assay for MRV, we were able to design a single set of primers based on the conserved regions in the L3 gene that can be used to amplify the same region in MRV types 1, 2 and 3. Non conserved nucleotides between the 3 serotypes were considered in the primer/probe synthesis and resulted in degenerate bases at one position in SEQ ID NO: 1 and at two positions in SEQ ID NO: 2 and SEQ ID NO: 3.

Reverse transcription is performed using MRV specific primers which reverse transcribe all reovirus types and both RNA strands with comparable efficacy. Both primers and the probe were tested for potential nonspecific binding to other RNA/DNA sequences which could result in a nonspecific PCR product, using the "BLAST" algorithm (BLASTN 2.2.16).

In the probe, a locked nucleic acid (LNA; mRV_LNA2) was used to achieve efficient annealing in the conserved region of all three MRV subtypes. Primer and probe concentrations of the assay were optimized to provide efficient amplification and fluorescence detection. Detailed primer and probe sequences are given in table 1. An overview of the primer and probe target region is shown in FIG. 2.

Specificity

Specificity of the assay was tested with all three MRV serotypes: MRV-1, strain Lang (ATCC VR-230); MRV-2, strain D5/Jones (ATCC VR-231); MRV-3 strain Dearing (ATCC VR-824) and MRV-3 strain Abney (ATCC VR-232). Reference strains were obtained from the American Type Culture Collection (ATCC).

Mammalian reoviruses with unknown sequences (typed by EM and serologically) were tested to prove specificity of this assay for more recent field isolates and non human strains. These included a porcine (strain Stendal 41/03 MRV-1), a bovine isolate (strain Riems 1/1991 MRV-1), an isolate of unknown origin (strain Riems 3/1991 MRV-3), and a porcine isolate (strain "Erik" MRV-1). All MRV strains were detected by the assay.

In addition six high titer (≥6.4 TCID50/ml) cell culture (BHK-cells) supernatants of avian reovirus field isolates or reference strains (ARV 8474; ARV K670; ARV F2-KN/ 1977; ARV Uchida/1977; ARV TS-17-9/1977; ARV S1133 UConn) tested negative when these were checked for potential cross reactivity with MRV.

These results demonstrate the high specificity of the methods, primers and probes of the invention.

Sensitivity

The sensitivity of the method was analyzed by duplicate determinations of 10-fold serial dilutions in water of MRV 1, 2 and 3 preparations with known infectivity titers. The PCR assays were performed according to the present invention.

Detailed results are given in Tables 2, 3, 4 and 5 and show positive results down to virus titers of 80-200 MRV TCID$_{50}$/ml for all four strains (3 types).

These data indicate that 80-200 MRV TCID$_{50}$/ml can be detected by the PCR. This would compare to 16-40 RNA copies/PCR reaction, considering that 1000 μl of the sample is used for RNA isolation, the isolated RNA is resuspended in 50 μl elution buffer, and 10 μl of this RNA is used in the one step real-time RT-PCR setup.

For exclusion of matrix effects due to influenza cell culture media (CDM/PF medium mixture) or influenza virus, we tested all 3 MRV serotypes in 10 fold serial dilutions of titered reovirus stocks. For these studies other preparations than those used above (see Tables 3-5) were applied. The results of these interference/sensitivity tests are summarized below in Tables 6-8. The data indicate that 35-631 MRV TCID$_{50}$/ml can be detected by PCR, independent of the sample matrix. There is no obvious inhibition of the assay by influenza viruses, remaining host cell proteins or by the media used to grow the influenza virus.

Testing of Seed Virus Samples

The newly developed assay was evaluated with Optaflu™ virus seeds or with parallel or, when material was limited, earlier passages of seed virus preparations. The assays were performed in triplicate. The results are summarized in Table 9. All 12 different influenza seed viruses for Optaflu™ were negative for MRV by PCR.

Conclusion

Specificity of this newly developed PCR assay was shown for MRV serotypes 1, 2, 3 with four reference viruses of ATCC origin. Additional four MRV field isolates were tested positive with this PCR assay. Six related avian reoviruses were tested negative, proving high specificity of the method, in particular when using the TaqMan qRT-PCR assay design. Due to the utilization of a specific probe and not only a specific primer pair we ensure that nonspecific PCR products are not detected. The achieved performance of the assay is sufficient to ensure the sensitive detection of 35-631 TCID$_{50}$/ml MRV in influenza virus infected cell culture supernatants and seed viruses. Thus, the present invention provides a specific and sensitive generic assay for the detection of all MRV types, subtypes and strains.

It will be understood that the invention has been described by way of example only and modifications may be made whilst remaining within the scope and spirit of the invention.

TABLE 1 preferred primer and probe sequences for the detection of MRV-1, MRV-2 and MRV-3. The probe sequences are Taqman ™ probes.

| SEQ ID NO | Name (primer/probe) | Sequence |
|---|---|---|
| 1 | mRV_BR1F | CACACKTGGCCACGATGC |
| 2 | mRV_rev | CTATGAATAATYTCRGCCCACTGTC |
| 3 | mRV_LNA2 | 6FAM-ATTT + CK + C + CAAT + CGAYG + CT + CC--BBQ |

+ C represents a cytosine with a 2'-O, 4'-C methylene bridge in its ribose

TABLE 2

Sensitivity evaluation of the developed PCR against MRV-1

| Sample | log10 $TCID_{50}$/mL | PCR result ($C_t$) |
|---|---|---|
| MRV-1 Lang VR-230 | 5.3 | positive (19.79/19.66) |
| MRV-1 Lang VR-230 | 4.3 | positive (24.29/24.32) |
| MRV-1 Lang VR-230 | 3.3 | positive (28.72/28.46) |
| MRV-1 Lang VR-230 | 2.3 | positive (35.63/33.14) |
| MRV-1 Lang VR-230 | 1.3 | negative (0/0) |
| MRV-1 Lang VR-230 | 0.3 | negative (0/0) |

The original virus harvest of MRV-1, strain Lang, (roller bottles cell culture supernatant; BH06-07-14) had a virus titer of 8.9 log10 $TCID_{50}$/mL and was diluted in distilled water to the titers given in table 2.

TABLE 3

Sensitivity evaluation of the developed PCR against MRV-2

| Sample | log10 $TCID_{50}$/mL | PCR result ($C_t$) |
|---|---|---|
| MRV-2 Jones VR-231 | 5.3 | positive (20.63/20.45) |
| MRV-2 Jones VR-231 | 4.3 | positive (25.33/25.59) |
| MRV-2 Jones VR-231 | 3.3 | positive (29.91/30.63) |
| MRV-2 Jones VR-231 | 2.3 | positive/negative (35.68/0) |
| MRV-2 Jones VR-231 | 1.3 | negative (0/0) |
| MRV-2 Jones VR-231 | 0.3 | negative (0/0) |

The original virus harvest of MRV-2 strain Jones (roller bottles cell culture supernatant; BH06-07-14) had a virus titer of 6.95 log10 $TCID_{50}$/mL and was diluted in distilled water to the titers given in table 3.

TABLE 4

Sensitivity evaluation of the developed PCR against MRV-3

| Sample | log10 $TCID_{50}$/mL | PCR result ($C_t$) |
|---|---|---|
| MRV-3 Dearing VR-824 | 5.3 | positive (17.41/17.51) |
| MRV-3 Dearing VR-824 | 4.3 | positive (22.32/21.90) |
| MRV-3 Dearing VR-824 | 3.3 | positive (26.59/26.42) |
| MRV-3 Dearing VR-824 | 2.3 | positive (30.96/30.95) |
| MRV-3 Dearing VR-824 | 1.3 | negative (0/0) |
| MRV-3 Dearing VR-824 | 0.3 | negative (0/0) |

The original virus harvest of MRV-3 strain Dearing (roller bottles cell culture supernatant; BH06-07-14) had a virus titer of 9.5 log10 $TCID_{50}$/mL and was diluted in distilled water to the titers given in table 4.

TABLE 5

Sensitivity evaluation of the developed PCR against MRV-3

| Sample | log10 $TCID_{50}$/mL | PCR result ($C_t$) |
|---|---|---|
| MRV-3 Abney VR-232 | 6.9 | positive (15.76/16.18) |
| MRV-3 Abney VR-232 | 5.9 | positive (19.08/19.21) |
| MRV-3 Abney VR-232 | 4.9 | positive (22.15/22.51) |
| MRV-3 Abney VR-232 | 3.9 | positive (23.82/24.32) |
| MRV-3 Abney VR-232 | 2.9 | positive (28.14/27.34) |
| MRV-3 Abney VR-232 | 1.9 | positive (32.31/31.78) |
| MRV-3 Abney VR-232 | 0.9 | negative (0/0) |
| MRV-3 Abney VR-232 | −0.1 | negative (0/0) |

The original virus harvest of MRV-3 strain Abney (cell culture supernatant 48 hpi; 29.10.99 from L 929) had a virus titer of 7.9 log10 $TCID_{50}$/mL and was diluted in distilled water to the titers given in table 5.

TABLE 6

Sensitivity of the developed PCR against MRV-1 in different matrixes

| MRV-1 RV706-39 log10 $TCID_{50}$/mL | Dilutions in CDM/PF medium PCR result (Ct) KS06-07-04 | Dilutions in influenza A cell culture supernatants (B1) PCR result (Ct) KS06-07-13 | Dilutions in influenza B cell culture supernatants (B1) PCR result (Ct) KS06-07-10 |
|---|---|---|---|
| 6.80 | positive (13.29/13.27) | not tested | not tested |
| 5.80 | positive (17.21/17.32) | positive (17.58/17.41) | positive (17.22/17.21) |
| 4.80 | positive (21.92/21.86) | positive (22.12/21.95) | positive (21.59/21.63) |
| 3.80 | positive (26.52/26.46) | positive (26.65/26.26) | positive (25.86/25.57) |
| 2.80 | positive (30.24/30.78) | positive (31.17/31.46) | positive (30.59/30.48) |
| 1.80 | negative (0/0) | negative (0/0) | negative(0/0) |
| 0.80 | negative (0/0) | not tested | not tested |

The original virus harvest of MRV-1 strain Lang (cell culture supernatant RV706-39) had a virus titer of 6.8 log10 $TCID_{50}$/mL, and was diluted in CDM/PF medium or cell culture supernatant of influenza A virus of 8.1 log10 $TCID_{50}$/mL (A/Bayern/7/95 ZK048 Ch271106) or influenza B virus of 7.9 log10 $TCID_{50}$/mL (B/Baden-Wurttemberg/3/06 ZK058 Ch271106).

TABLE 7

Comparison of sensitivity of the developed PCR against MRV-2 in different matrixes

| MRV-2 RV706-40 log10 $TCID_{50}$/mL | Dilutions in CDM/PF medium PCR result ($C_t$) KS06-07-04 | Dilutions in influenza A cell culture supernatants (B1) PCR result ($C_t$) KS06-07-14 | Dilutions in influenza B cell culture supernatants (B1) PCR result ($C_t$) KS06-07-11 |
|---|---|---|---|
| 6.75 | positive (12.90/12.85) | not tested | not tested |
| 5.75 | positive (17.50/17.14) | positive (17.61/17.74) | positive (18.10/17.68) |
| 4.75 | positive (21.46/21.34) | positive (22.46/21.99) | positive (22.99/22.55) |
| 3.75 | positive (26.16/26.38) | positive (27.25/27.09) | positive (27.66/27.44) |
| 2.75 | positive (31.36/31.16) | positive (32.18/32.20) | positive (31.83/32.32) |
| 1.75 | negative (0/0) | negative (0/0) | negative (0/0) |
| 0.75 | negative (0/0) | not tested | not tested |

The original virus harvest of MRV-2 strain Jones (cell culture supernatant RV706-40) had a virus titer of 6.75 log10 $TCID_{50}$/mL and was diluted in CDM/PF medium or cell culture supernatant of influenza A virus of 8.1 log10 $TCID_{50}$/mL (A/Bayern/7/95 ZK048 Ch271106) or influenza B virus of 7.9 log10 $TCID_{50}$/mL (B/Baden-Wurttemberg/3/06 ZK058 Ch271106).

TABLE 8

Comparison of sensitivity of the developed PCR against MRV-3 in different matrixes

| MRV-3 RV706-41 log10 $TCID_{50}$/mL | Dilutions in CDM/PF medium PCR result ($C_t$) KS06-07-05 | Dilutions in influenza A cell culture supernatants (B1) PCR result ($C_t$) KS06-07-14 | Dilutions in influenza B cell culture supernatants (B1) PCR result ($C_t$) KS06-07-11 |
|---|---|---|---|
| 6.55 | positive (12.45/12.26) | not tested | not tested |
| 5.55 | positive (16.52/16.34) | positive (17.16/16.76) | positive (17.12/16.77) |
| 4.55 | positive (20.46/20.58) | positive (21.94/21.35) | positive (21.47/21.25) |
| 3.55 | positive (24.58/24.29) | positive (25.54/25.66) | positive (25.59/25.66) |
| 2.55 | positive (29.08/28.87) | positive (29.79/30.22) | positive (29.71/29.67) |
| 1.55 | positive (34.56/35.80) | negative/positive (0/35.71) | negative/positive (0/34.74) |
| 0.55 | negative (0/0) | not tested | not tested |

The original virus harvest of MRV-3 strain Dearing (cell culture supernatant RV706-41) had a virus titer of 6.55 log10 $TCID_{50}$/mL and was diluted in CDM/PF medium or cell culture supernatant of influenza A virus of 8.1 log10 $TCID_50$/mL (A/Bayern/7/95 ZK048 Ch271106) or influenza B virus of 7.9 log10 $TCID_{50}$/mL (B/Baden-Wurttemberg/3/06 ZK058 Ch271106).

TABLE 9

Results of MRV PCR tests of Optaflu ™ seed virus preparations.

| Influenza virus, seed lot | Ct | Result |
|---|---|---|
| B/BW/B/Jiangsu-like, Ch150906 SV0603 | 0.00 | negative |
| B/BW/B/Jiangsu-like, Ch150906 SV0603 | 0.00 | negative |

TABLE 9-continued

Results of MRV PCR tests of Optaflu ™ seed virus preparations.

| Influenza virus, seed lot | Ct | Result |
|---|---|---|
| B/BW/B/Jiangsu-like, Ch150906 SV0603 | 0.00 | negative |
| A/Wyoming, Ch220104 ZK080304 | 0.00 | negative |

TABLE 9-continued

Results of MRV PCR tests of Optaflu ™ seed virus preparations.

| Influenza virus, seed lot | Ct | Result |
|---|---|---|
| A/Wyoming, Ch220104 ZK080304 | 0.00 | negative |
| A/Wyoming, Ch220104 ZK080304 | 0.00 | negative |

TABLE 9-continued

Results of MRV PCR tests of Optaflu™ seed virus preparations.

| Influenza virus, seed lot | Ct | Result |
|---|---|---|
| A/Wellington, Ch081004 ZK051104 | 0.00 | negative |
| A/Wellington, Ch081004 ZK051104 | 0.00 | negative |
| A/Wellington, Ch081004 ZK051104 | 0.00 | negative |
| B/Malaysia, Ch071005 ZK241005 | 0.00 | negative |
| B/Malaysia, Ch071005 ZK241005 | 0.00 | negative |
| B/Malaysia, Ch071005 ZK241005 | 0.00 | negative |
| B/Guandong, ZK140901 Spinner1a* | 0.00 | negative |
| B/Guandong, ZK140901 Spinner1a* | 0.00 | negative |
| B/Guandong, ZK140901 Spinner1a* | 0.00 | negative |
| B/Shangdong, Ch020603 ZK021 | 0.00 | negative |
| B/Shangdong, Ch020603 ZK021 | 0.00 | negative |
| B/Shangdong, Ch020603 ZK021 | 0.00 | negative |
| A/Panama, Ch230701 ZK190503/2 | 0.00 | negative |
| A/Panama, Ch230701 ZK190503/2 | 0.00 | negative |
| A/Panama, Ch230701 ZK190503/2 | 0.00 | negative |
| A/Wisconsin X-161-B, 522SSV0601 | 0.00 | negative |
| A/Wisconsin X-161-B, 522SSV0601 | 0.00 | negative |
| A/Wisconsin X-161-B, 522SSV0601 | 0.00 | negative |
| A/Solomon, 522SSV0701 | 0.00 | negative |
| A/Solomon, 522SSV0701 | 0.00 | negative |
| A/Solomon, 522SSV0701 | 0.00 | negative |
| B/Jiangsu, CH050404 ZK012* | 0.00 | negative |
| B/Jiangsu, CH050404 ZK012* | 0.00 | negative |
| B/Jiangsu, CH050404 ZK012* | 0.00 | negative |
| A/New York X-157, CH110305 ZK014* | 0.00 | negative |
| A/New York X-157, CH110305 ZK014* | 0.00 | negative |
| A/New York X-157, CH110305 ZK014* | 0.00 | negative |
| A/New Caledonia, CH161105 ZK241105/2 | 0.00 | negative |
| A/New Caledonia, CH161105 ZK241105/2 | 0.00 | negative |
| A/New Caledonia, CH161105 ZK241105/2 | 0.00 | negative |

Released seed virus lots for Optaflu™ or, due to limited availability for evaluation purposes, parallel or earlier passages of seed virus preparations (marked with *) were analyzed in triplicate

REFERENCES

[1] WO 2006/027698
[2] Leary et al. (2002) J Clin Microbiol; 40(4):1368-75
[3] Spinner and Di Giovanni (2001) Appl Environ Microbiol.; 67(7):3016-20
[4] Wilschut; Mc Elhaney, Palache in "Influenza"; 2. Edition; Elsevier 2006; ISBN 0-7234-3433-6 Chapter 9
[5] WO 2008/068631
[6] Huckriede et al. (2003) *Methods Enzymol* 373:74-91.
[7] Greenbaum et al. (2004) *Vaccine* 22:2566-77.
[8] Zurbriggen et al. (2003) *Expert Rev Vaccines* 2:295-304.
[9] Piascik (2003) *J Am Pharm Assoc* (Wash D.C.). 43:728-30.
[10] Mann et al. (2004) *Vaccine* 22:2425-9.
[11] Halperin et al. (1979) *Am J Public Health* 69:1247-50.
[12] Herbert et al. (1979) *J Infect Dis* 140:234-8.
[13] Chen et al. (2003) *Vaccine* 21:2830-6.
[14] Hehme et al. (2004) *Virus Res* 103:163-71.
[15] U.S. Pat. No. 6,372,223.
[16] U.S. Pat. No. 6,534,065.
[17] Cooper et al. (2004) *Vaccine* 22:3136-43.
[18] Frey et al. (2003) *Vaccine* 21:4234-7.
[19] Bozkir & Hayta (2004) *Drug Target* 12:157-64.
[20] Guebre-Xabier et al. (2003) *J Virol* 77:5218-25.
[21] Peppoloni et al. (2003) *Expert Rev Vaccines* 2:285-93.
[22] Pine et al. (2002) *J Control Release* 85:263-70.
[23] Baldridge et al. (2000) *Vaccine* 18:2416-25.
[24] WO94/19013.
[25] EP-A-0721782.
[26] U.S. Pat. No. 5,292,506.
[27] WO 01/22992.
[28] Banzhoff (2000) *Immunology Letters* 71:91-96.
[29] WO 02/097072.
[30] Knipe & Howley *Fields Virology* (4th edition, 2001). ISBN 0-7817-1832-5.
[31] *Current Protocols in Molecular Biology* (F. M. Ausubel et al., eds., 1987) Supplement 30
[32] Smith and Waterman, Adv. Appl. Math. (1981) 2: 482-489.

The invention claimed is:

1. A method for detecting the presence or absence of mammalian reovirus (MRV) RNA in a sample, comprising the steps of:

(i) performing a real time (qPCR) nucleic acid assay using a primer pair, wherein each primer in said primer pair hybridizes to the mammalian reovirus L3 inner capsid nucleic acid sequence recited in SEQ ID NO: 8 or its complement; to produce an MRV amplification product if MRV RNA is present in the sample; and (ii) detecting the presence or absence of mammalian reovirus (MRV) RNA in the sample by detecting the presence or absence of the amplification product of step (i).

2. The method of claim 1, each primer of the primer pair hybridizes to SEQ ID NO: 5, 6 or 7 or the complements thereof.

3. The method of claim 1, each primer of the primer pair hybridizes to SEQ ID NO: 9, 10 or 11 or the complements thereof.

4. The method of claim 1, further comprising extracting RNA from the sample before performing the real time qPCR assay of step (i).

5. The method of claim 1, wherein the real time qPCR assay of step (i) is a one-step RT-qPCR.

6. The method of claim 4, wherein the real time qPCR assay of step (i) is a one-step RT-qPCR.

7. The method of claim 5, wherein the real time qPCR assay is performed with a primer selected from the group consisting of SEQ ID NO: 1 and SEQ ID NO: 2.

8. The method of claim 6, wherein the amplification product is detected using a probe of SEQ ID NO: 3.

9. A method for detecting MRV RNA in a sample comprising the steps of:
   (a) extracting RNA from the sample;
   (b) performing a real time (qPCR) assay by contacting the RNA extracted in step (a) with a primer pair and a probe to produce an MRV amplification product if MRV RNA is present in the sample, wherein each primer in said primer pair hybridizes to SEQ ID NO: 8 or its complement and at least one of SEQ ID NOS: 1, 2 and 3 is used in the qPCR assay; and
   (c) detecting the presence or absence of MRV RNA in the sample by detecting the presence or absence of the amplification product of step (b).

10. The method of claim 4, wherein the sample is an influenza vaccine or an intermediate in the manufacture of an influenza vaccine.

11. The method of claim 10, wherein the intermediate in the manufacture of an influenza vaccine is a seed virus, cell substrate, culture medium, and/or viral harvest.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Forward Primer mRV BR1F
<220> FEATURE:
<221> NAME/KEY: misc_feature
<222> LOCATION: (6)..(6)
<223> OTHER INFORMATION: g or t

<400> SEQUENCE: 1
cacacktggc cacgatgc                                                 18

<210> SEQ ID NO 2
<211> LENGTH: 25
<212> TYPE: DNA
<213> ORGANISM: Artificial Sequence
<220> FEATURE:
<223> OTHER INFORMATION: Reverse Primer mRV_rev
<220> FEATURE:
<221> NAME/KEY: misc_feature
<222> LOCATION: (12)..(12)
<223> OTHER INFORMATION: t or c
```

-continued

```
<220> FEATURE:
<221> NAME/KEY: misc_feature
<222> LOCATION: (15)..(15)
<223> OTHER INFORMATION: g or a

<400> SEQUENCE: 2
ctatgaataa tytcrgccca ctgtc                                           25

<210> SEQ ID NO 3
<211> LENGTH: 20
<212> TYPE: DNA
<213> ORGANISM: Artificial Sequence
<220> FEATURE:
<223> OTHER INFORMATION: Taqman probe
<220> FEATURE:
<221> NAME/KEY: misc_feature
<222> LOCATION: (5)..(5)
<223> OTHER INFORMATION: Bridged nucleic acid
<220> FEATURE:
<221> NAME/KEY: misc_feature
<222> LOCATION: (6)..(6)
<223> OTHER INFORMATION: g or t
<220> FEATURE:
<221> NAME/KEY: misc_feature
<222> LOCATION: (7)..(7)
<223> OTHER INFORMATION: Bridged nucleic acid
<220> FEATURE:
<221> NAME/KEY: misc_feature
<222> LOCATION: (8)..(8)
<223> OTHER INFORMATION: Bridged nucleic acid
<220> FEATURE:
<221> NAME/KEY: misc_feature
<222> LOCATION: (12)..(12)
<223> OTHER INFORMATION: Bridged nucleic acid
<220> FEATURE:
<221> NAME/KEY: misc_feature
<222> LOCATION: (15)..(15)
<223> OTHER INFORMATION: t or c
<220> FEATURE:
<221> NAME/KEY: misc_feature
<222> LOCATION: (17)..(17)
<223> OTHER INFORMATION: Bridged nucleic acid
<220> FEATURE:
<221> NAME/KEY: misc_feature
<222> LOCATION: (19)..(19)
<223> OTHER INFORMATION: Bridged nucleic acid

<400> SEQUENCE: 3
atttckccaa tcgaygctcc                                                 20

<210> SEQ ID NO 4
<211> LENGTH: 89
<212> TYPE: DNA
<213> ORGANISM: Artificial Sequence
<220> FEATURE:
<223> OTHER INFORMATION: Amplified Region
<220> FEATURE:
<221> NAME/KEY: misc_feature
<222> LOCATION: (6)..(6)
<223> OTHER INFORMATION: g or t
<220> FEATURE:
<221> NAME/KEY: misc_feature
<222> LOCATION: (21)..(21)
<223> OTHER INFORMATION: t or c
<220> FEATURE:
<221> NAME/KEY: misc_feature
<222> LOCATION: (27)..(27)
<223> OTHER INFORMATION: t or c
<220> FEATURE:
<221> NAME/KEY: misc_feature
<222> LOCATION: (30)..(30)
<223> OTHER INFORMATION: a or c
<220> FEATURE:
<221> NAME/KEY: misc_feature
<222> LOCATION: (33)..(33)
```

<223> OTHER INFORMATION: g or a
<220> FEATURE:
<221> NAME/KEY: misc_feature
<222> LOCATION: (36)..(36)
<223> OTHER INFORMATION: g or a
<220> FEATURE:
<221> NAME/KEY: misc_feature
<222> LOCATION: (42)..(42)
<223> OTHER INFORMATION: g or t
<220> FEATURE:
<221> NAME/KEY: misc_feature
<222> LOCATION: (51)..(51)
<223> OTHER INFORMATION: t or c
<220> FEATURE:
<221> NAME/KEY: misc_feature
<222> LOCATION: (57)..(57)
<223> OTHER INFORMATION: a or c or t
<220> FEATURE:
<221> NAME/KEY: misc_feature
<222> LOCATION: (61)..(61)
<223> OTHER INFORMATION: t or c
<220> FEATURE:
<221> NAME/KEY: misc_feature
<222> LOCATION: (64)..(64)
<223> OTHER INFORMATION: a or c
<220> FEATURE:
<221> NAME/KEY: misc_feature
<222> LOCATION: (75)..(75)
<223> OTHER INFORMATION: t or c
<220> FEATURE:
<221> NAME/KEY: misc_feature
<222> LOCATION: (78)..(78)
<223> OTHER INFORMATION: g or a

<400> SEQUENCE: 4
cacacktggc cacgatgctt yatgaayatm carttrattt ckccaatcga ygctcchatc 60
ytgmgacagt gggcygarat tattcatag 89

<210> SEQ ID NO 5
<211> LENGTH: 137
<212> TYPE: DNA
<213> ORGANISM: Reovirus 1, strain Lang

<400> SEQUENCE: 5
tcaatcgaga cgcgcgagtg ctttctcaac gcctcacacg tggccacgat gcttcatgaa 60
tatccagtta atttctccaa tcgatgctcc tatcttgcga cagtgggctg aaattattca 120
tagatacggc ctaaccc 137

<210> SEQ ID NO 6
<211> LENGTH: 137
<212> TYPE: DNA
<213> ORGANISM: Reovirus 2, strain Jones

<400> SEQUENCE: 6
tcaatcacgg agagctagcg cgttttccac tccccacact tggccacgat gctttatgaa 60
catacaattg atttcgccaa tcgacgctcc aatcctgaga cagtgggccg agattattca 120
tagatacggc cgaatcc 137

<210> SEQ ID NO 7
<211> LENGTH: 137
<212> TYPE: DNA
<213> ORGANISM: Reovirus 3, strain Dearing

<400> SEQUENCE: 7
tcaatcgaga cgcgcgagtg ctttctcaac gcctcacacg tggccacgat gctttatgaa 60
catccagtta atttctccaa tcgacgctcc catcttgcga cagtgggctg aaattattca 120

```
tagatacggc taaccc                                               137

<210> SEQ ID NO 8
<211> LENGTH: 138
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (91)..(91)
<223> OTHER INFORMATION: a or c or t

<400> SEQUENCE: 8
tcaatcgaga cgcgcgagtg ctttctcaac gcctcacacg tggccacgat gctttatgaa    60
catccagtta atttctccaa tcgacgctcc hatcttgcga cagtgggctg aaattattca   120
tagatactgg cctaaccc                                                 138

<210> SEQ ID NO 9
<211> LENGTH: 138
<212> TYPE: DNA
<213> ORGANISM: Reovirus 1, strain Lang

<400> SEQUENCE: 9
tcaatcgaga cgcgcgagtg ctttctcaac gcctcacacg tggccacgat gcttcatgaa    60
tatccagtta atttctccaa tcgatgctcc tatcttgcga cagtgggctg aaattattca   120
tagatactgg cctaaccc                                                 138

<210> SEQ ID NO 10
<211> LENGTH: 138
<212> TYPE: DNA
<213> ORGANISM: Reovirus 2, strain Jones

<400> SEQUENCE: 10
tcaatcacgg agagctagcg cgttttccac tccccacact tggccacgat gctttatgaa    60
catacaattg atttcgccaa tcgacgctcc aatcctgaga cagtgggccg agattattca   120
tagatactgg ccgaatcc                                                 138

<210> SEQ ID NO 11
<211> LENGTH: 138
<212> TYPE: DNA
<213> ORGANISM: Reovirus 3, strain Dearing

<400> SEQUENCE: 11
tcaatcgaga cgcgcgagtg ctttctcaac gcctcacacg tggccacgat gctttatgaa    60
catccagtta atttctccaa tcgacgctcc catcttgcga cagtgggctg aaattattca   120
tagatactgg cctaaccc                                                 138
```